United States Patent [19]

Bosch et al.

[11] Patent Number: 5,087,746

[45] Date of Patent: Feb. 11, 1992

[54] PROCESS FOR THE PRODUCTION OF HIGH PURITY TARTARIC ACID

[75] Inventors: Richard J. Bosch, Creve Coeur; Skippy H. Ramsey, Fenton, both of Mo.

[73] Assignee: Monsanto Company, St. Louis, Mo.

[21] Appl. No.: 652,498

[22] Filed: Feb. 11, 1991

Related U.S. Application Data

[63] Continuation of Ser. No. 72,375, Jul. 13, 1987, abandoned.

[51] Int. Cl.$^5$ ............................................. C07C 59/155
[52] U.S. Cl. ..................................................... 562/585
[58] Field of Search .......................................... 562/585

[56] References Cited

U.S. PATENT DOCUMENTS

| | | |
|---|---|---|
| 3,156,709 | 11/1964 | Allan ................................. 549/531 |
| 3,769,339 | 10/1973 | Wagner et al. ..................... 562/585 |
| 3,875,223 | 4/1975 | Yonemitsu et al. ................. 562/585 |
| 3,923,884 | 12/1975 | Yonemitsu et al. ................. 562/585 |
| 4,028,407 | 6/1977 | Petritsch et al. ................... 562/585 |
| 4,048,225 | 9/1977 | Prescher et al. ................... 562/585 |

*Primary Examiner*—Bruce Gray
*Attorney, Agent, or Firm*—R. C. Loyer

[57] ABSTRACT

Disodium tartrate which can be easily converted to tartaric acid is produced by hydrolysis of an epoxysuccinate. Formation of impurities is minimized and the reaction time shortened by performing the hydrolysis under superatmospheric pressure and elevated temperature at a pH in the range of from about 6 to about 11.

8 Claims, No Drawings

PROCESS FOR THE PRODUCTION OF HIGH PURITY TARTARIC ACID

This is a continuation of application Ser. No. 07/072,375, filed on July 13, 1987, now abandoned.

This invention relates to a process for the production of d,1-tartaric acid and more particularly to an improved process for the hydrolysis of an epoxysuccinate.

Tartaric acid and its salts, particularly the racemic mixture, have been employed for many years as intermediates in the organic chemical industry to provide food and drug products. Uses for tartaric acid not only in the food and drug industry but also in the detergent industry have created an increasing demand for the product in racemic mixture thereby creating interest in efficient methods for synthesis processes avoiding the formation of impurities.

Tartrate salts have been synthesized by epoxidation of maleic or fumaric acid or their salts followed by hydrolysis. Typically the reaction is carried out in the liquid phase with the aid of a catalyst. An example of such synthesis procedure is found in U.S. Pat. No. 3,156,709 to Allen wherein it is taught that improved yields are obtained by employing certain catalysts comprising organometallic compounds in alkaline reaction medium. However, as a result of the continued study of synthesis procedures, metal oxides, particularly tungsten containing compounds, were found to be superior catalysts for the epoxidation of the starting acid. Because hydrolysis is conveniently performed immediately after epoxidation, the hydrolysis is carried out at the same relatively low pH levels as epoxidation.

It is widely known that epoxysuccinate salts are easily hydrolyzed at either low pH of in the range of from about 1 to 5.5 or high pH of above about 11. However, such hydrolysis product contains undesired impurities. One such hydrolysis process is disclosed in U.S. Pat. No. 3,769,339 to Wagner et al. In the usual procedure the epoxide is boiled at atmospheric pressure to achieve hydrolysis. Various catalysts have been suggested for the hydrolysis of epoxysuccinic acids such aluminum, iron, tin or bismuth. A catalyzed process is performed at or near the atmospheric reflux temperature of an aqueous solution of epoxysuccinic acid. Such a process is described in U.S. Pat. No. 3,875,223 to Yonemitsu et al.

One attempt to decrease the objectionable impurities obtained by the hydrolysis of epoxysuccinate to d,1-tartaric acid is described in U.S. Pat. No. 4,028,407 to Petritsch. In the approach toward purity of product taken by this patentee, tartaric acid was obtained by first epoxidizing calcium acid maleate in the usual manner with a tungsten acid-containing catalyst and reacting the resulting calcium acid epoxysuccinate with sulfuric acid to form a calcium sulfate and epoxysuccinic acid. An organic solvent is employed either alone or with water as a medium in which to react the calcium epoxysuccinate with sulfuric acid to obtain calcium sulfate and epoxysuccinic acid. The epoxysuccinic acid is hydrolyzed in the usual manner by boiling an aqueous solution at low pH to provide the desired tartaric acid.

It is known that epoxysuccinic acid or its salts are easily hydrolyzed in either strongly acid or strongly basic media. However, under more mild reaction conditions such as in a range of about pH 7, it takes a long time to carry out the reaction and obtain high yield. Accordingly, there is desired an industrially advantageous process producing d,1-tartaric acid from epoxysuccinic acid in a very short time with good conversion as well as selectivity at mild reaction conditions of pH and temperature.

SUMMARY OF THE INVENTION

In accordance with this invention, there is provided a process for the production of d,1-tartaric acid or its alkali metal salts by the hydrolysis of epoxysuccinic acid or its salts under superatmospheric pressure at elevated temperatures in aqueous solution wherein the solution has a pH in the range of from about 6 to about 11. It has been found that reaction time is convenient while the product is provided in high purity under these conditions.

DETAILED DESCRIPTION OF THE INVENTION

The epoxysuccinic acid used as the starting material for the process of this invention may be produced in any way. It may be produced according to known methods as mentioned above by allowing hydrogen peroxide to react with maleic acid in aqueous solution in the presence of a tungsten compound catalyst. In accordance with this invention it is preferable to employ the alkali metal salt of epoxysuccinic acid and more preferably the sodium salt. Any water soluble salt of epoxysuccinic may be employed however.

In accordance with this invention a mild basic hydrolysis reaction occurs by combining the epoxysuccinic acid or salt thereof with water under neutral to mildly alkaline conditions. While the reaction takes place in accordance with this invention at a pH in the range of from about 6 to about 11 it is preferred to utilize the higher end of the range of 9-10 and particularly a pH of 10 has been found to be most desirable.

By placing the hydrolysis reaction mixture under superatmospheric pressure and elevated temperature it has been found that the reaction proceeds quickly with greatly reduced undesired by-products. Any suitable pressure may be employed above atmospheric and it has been found desirable to operate the reaction in the range of up to about 70 psig. Typically, the process of this invention is conveniently operated at a pressure in the range of from about 50 psig-60 psig and more preferably about 55 psig.

It is self-evident that temperature and pressure have some relationship and therefore the operating temperature will influence the operating pressure to a great extent. Accordingly, the temperature at which the process of this invention is best suited covers a broad range of from about 105° C. near atmospheric pressure while conveniently temperatures of up to 200° C. may be employed at the higher end of the pressure range. It has been found most advantageous to operate the process at a temperature range of from about 140° C. to about 160° C. and more particularly preferred at about 150° C.

In the usual commercial operation the epoxysuccinic acid or salt thereof employed in the hydrolysis step is contained in aqueous solution with the reaction mixture resulting from the epoxidation step. The pH of the solution is adjusted by means of adding an alkali metal base such as sodium hydroxide so as to provide a pH in the range of from about 6 to about 11. The concentration of the epoxysuccinic acid in aqueous solution may range throughout any convenient amount and is usually an amount which provides a salt concentration in solution in the range of from about 20-50 percent by weight. More preferably the concentration of epoxysuccinate salt in aqueous solution is in the range of from about 30-35 percent by weight and preferably about 33 percent by weight.

Typical reaction time can range from several minutes to several days. In most instances, however, a reaction time of about one hour under elevated temperature and pressure is adequate to convert substantially all of the epoxysuccinate or epoxysuccinic acid to the desired d,1-tartaric acid or alkali metal tartrate. When operated in accordance with this invention, the hydrolysis of epoxysuccinic acid can provide up to 98 percent pure d,1-tartaric acid or alkali metal salt with 96 percent conversion of the epoxide. It has been found that by operating within the mild pH range of about 6 to about 11 the side products produced in the prior art at more severe pH levels, either lower or higher, are avoided. For example, the polyepoxysuccinate by-product normally produced at high pH is greatly reduced in the d,1-tartaric acid produced in accordance with this invention. Likewise, meso-tartrate usually appearing at low pH of about 1-5 is found to be reduced to low amounts in the product of the process of this invention.

The present invention is further illustrated with reference to the following examples wherein percent refers to weight percent unless otherwise noted.

EXAMPLE 1

A reaction product of a tungstate catalyzed expoxidation reaction containing 27% dissolved sodium epoxysucinate (mono- or di- depending upon final adjusted pH) and other products of the epoxidation step as well as catalyst was employed in various hydrolysis runs at a temperature of 150° C. and about 55 psig for 1 hour. The pH was adjusted to various levels by addition of either maleic anhydride or sodium hydroxide. The product of the hydrolysis reaction was analyzed by high pressure liquid chromatography (HPLC) to determine the amount of tartrate and various undesired by-products and starting epoxide in the hydrolysis product. The pH level in runs 1-5 show results at various pH levels and such results are presented in Table I below in relative weigh percent contained in the product.

TABLE I

| RUN | 1 | 2 | 3 | 4 | 5 |
|---|---|---|---|---|---|
| pH | 6.4 | 9.0 | 9.5 | 10.4 | 12.0 |
| HPLC Analysis: | | | | | |
| d,1-tartrate | 94.3 | 96.9 | 95.6 | 94.0 | 92.9 |
| meso-tartrate | 2.0 | 1.1 | 1.5 | 1.3 | 1.3 |
| PE[1] | 2.0 | 2.7 | 2.2 | 2.6 | 3.6 |
| Epoxide | 1.8 | 0.5 | 0.6 | 2.1 | 2.2 |

[1]polyepoxysuccinate

EXAMPLE 2

A reaction product of a tungstate catalyzed epoxidation reaction containing about 29% dissolved sodium epoxysuccinate and other products as well as the tungstate catalyst was subjected to hydrolysis after the pH of the solution was adjusted to 10. The hydrolysis was carried out at atmospheric pressure by refluxing the solution at about 105° C. for a period of 46.5 hours. The resulting hydrolysis product was analyzed by means of HPLC and found to contain, by relative weight percent, 98.2%, d,1-tartrate; 1% meso-tartrate; 0.4% polyepoxysuccinate and 0.3% epoxysuccinate.

EXAMPLE 3

The hydrolysis procedure of Example I was repeated in the following runs wherein the starting material contained about 34% sodium epoxysuccinate. The varying reaction conditions and HPLC analysis of the hydrolysis product are presented in Table II below employing various hydrolysis agents. The data in Table II were obtained by procedures wherein the pH was in the more severe range known in the prior art. In Table II a dashed line indicates the lack of appropriate data.

TABLE II

| RUN | 6 | 7 | 8 | 9 |
|---|---|---|---|---|
| Time (hrs) | 1.25 | 0.75 | 4 | 2 |
| Pressure | atm. | 5 psig | atm. | 18 psig |
| Agent- | NaOH | NaOH | formic acid | maleic acid |
| (moles) | 0.6 | 0.6 | — | — |
| pH | >12 | >12 | 4 | 4 |
| Temperature | reflux | | reflux | — |
| HPLC Analysis (relative wt. %) | | | | |
| d,1-tartrate | 83.7 | 78.4 | 92.3 | 91.0 |
| meso-tartrate | 4.2 | 7.8 | 4.5 | 6.0 |
| PE[1] | 11.3 | 13.8 | — | — |
| Epoxide | 0.8 | <1 | 3.2 | 3.0 |

[1]Polyepoxysuccinate

The above examples demonstrate the high conversion of an alkali metal epoxysuccinate to d,1-tartrate in a relatively short reaction time period. The sale produced can easily be converted to the acid by known means. The high conversion and shorter reaction time is complimented by the relatively lower amounts of side products that are produced at the more severe hydrolysis conditions known in the prior art.

While the invention has been described and claimed with respect to certain embodiments, such embodiments are not intended to limit the invention in any way. Various modifications and alterations may be made to the process claimed herein without departing from the spirit of the invention.

What is claimed is:

1. A process for producing d,1-tartaric acid alkali metal salt which comprises hydrolyzing an alkali metal epoxysuccinate in aqueous solution at a pH in the range of from about 6 to 11 at a temperature in the range of up to about 200° C. under superatmospheric pressure.

2. The process of claim 1 wherein the hydrolysis is allowed to proceed for about 1 hour.

3. The process of claim 1 wherein the pressure is in the range of up to 70 psig.

4. The process of claim 1 wherein the reaction temperature is in the range of from about 14020 C. to about 160° C.

5. The process of claim 1 wherein the pH is in the range of about 9-10.

6. The process of claim 3 wherein the pressure is in the range of from about 50 psig to about 60 psig.

7. The process of claim 1 wherein the aqueous solution is the reaction product of a tungsten catalyzed epoxidation reaction wherein maleic anhydride and aqueous hydrogen peroxide are combined to produce an epoxysuccinate.

8. The process of claim 1 wherein the alkali metal salt of the d,1-tartaric acid is the sodium salt.

* * * * *